US011253241B2

(12) United States Patent
Li

(10) Patent No.: US 11,253,241 B2
(45) Date of Patent: Feb. 22, 2022

(54) LEFT ATRIAL APPENDAGE OCCLUDER

(71) Applicant: LIFETECH SCIENTIFIC (SHENZHEN) CO., LTD, Shenzhen (CN)

(72) Inventor: Anning Li, Shenzhen (CN)

(73) Assignee: LIFETECH SCIENTIFIC (SHENZHEN) CO., LTD., Shenzhen (CN)

( * ) Notice: Subject to any disclaimer, the term of this patent is extended or adjusted under 35 U.S.C. 154(b) by 177 days.

(21) Appl. No.: 16/066,832

(22) PCT Filed: Jun. 17, 2016

(86) PCT No.: PCT/CN2016/086113
§ 371 (c)(1),
(2) Date: Jun. 28, 2018

(87) PCT Pub. No.: WO2017/113631
PCT Pub. Date: Jul. 6, 2017

(65) Prior Publication Data
US 2019/0008495 A1 Jan. 10, 2019

(30) Foreign Application Priority Data
Dec. 31, 2015 (CN) .......................... 201511033727.0

(51) Int. Cl.
*A61B 17/00* (2006.01)
*A61B 17/12* (2006.01)
*A61F 2/04* (2013.01)

(52) U.S. Cl.
CPC .... *A61B 17/0057* (2013.01); *A61B 17/12031* (2013.01); *A61B 17/12122* (2013.01);
(Continued)

(58) Field of Classification Search
CPC .......... A61B 17/0057; A61B 17/12122; A61B 17/12031
See application file for complete search history.

(56) References Cited

U.S. PATENT DOCUMENTS

| 5,944,738 A | * | 8/1999 | Amplatz | ............ | A61B 17/0057 |
| | | | | | 606/213 |
| 7,972,359 B2 | * | 7/2011 | Kreidler | ............. | A61B 17/0057 |
| | | | | | 606/213 |

(Continued)

FOREIGN PATENT DOCUMENTS

| CN | 102805654 A | 12/2012 |
| CN | 103598902 A | 2/2014 |

(Continued)

OTHER PUBLICATIONS

International Search Report dated Sep. 26, 2016 of corresponding International Application No. PCT/CN2016/086113; 6 pgs.

(Continued)

*Primary Examiner* — Melanie R Tyson
*Assistant Examiner* — Mohammed S Adam
(74) *Attorney, Agent, or Firm* — Maier & Maier, PLLC

(57) ABSTRACT

A left atrial appendage occluder, including a closure disc, a bracket located on one side of the closure disc, and a connecting member connecting the closure disc and the bracket; the bracket includes a first fixing connection member, a second fixing connection member, and a number of support rods; the first ends of the plurality of support rods are collapsed and secured by the first fixing connection member; the second ends of the plurality of support rods are collapsed and secured by the second fixing connection member; a connecting member is connected to the first fixing connection member. The bracket is arranged such that the two ends constituted by at least two support rods have a (Continued)

closed structure, thus increasing the area of contact between the outer surface of the bracket and the left atrial appendage.

20 Claims, 7 Drawing Sheets

(52) U.S. Cl.
CPC .. *A61B 17/12145* (2013.01); *A61B 17/12172* (2013.01); *A61F 2/04* (2013.01); *A61B 17/12177* (2013.01); *A61B 2017/0061* (2013.01); *A61B 2017/00526* (2013.01); *A61B 2017/00592* (2013.01); *A61B 2017/00606* (2013.01); *A61B 2017/00615* (2013.01); *A61B 2017/00632* (2013.01)

(56) References Cited

U.S. PATENT DOCUMENTS

| | | | | |
|---|---|---|---|---|
| 8,366,743 | B2* | 2/2013 | Zeng | A61B 17/0057 606/213 |
| 9,808,253 | B2* | 11/2017 | Li | A61B 17/12122 |
| 2002/0111647 | A1* | 8/2002 | Khairkhahan | A61B 17/0057 606/200 |
| 2003/0220667 | A1* | 11/2003 | van der Burg | A61B 17/0057 606/200 |
| 2004/0093017 | A1* | 5/2004 | Chanduszko | A61B 17/0057 606/200 |
| 2005/0043759 | A1* | 2/2005 | Chanduszko | A61B 17/0057 606/213 |
| 2005/0177182 | A1* | 8/2005 | van der Burg | A61B 17/0057 606/157 |
| 2007/0032820 | A1* | 2/2007 | Chin-Chen | A61B 17/0057 606/213 |
| 2007/0066993 | A1* | 3/2007 | Kreidler | A61B 17/0057 606/213 |
| 2007/0265656 | A1* | 11/2007 | Amplatz | A61B 17/0057 606/200 |
| 2008/0033421 | A1* | 2/2008 | Davis | A61B 17/0057 606/28 |
| 2009/0018562 | A1* | 1/2009 | Amplatz | A61B 17/0057 606/157 |
| 2009/0099647 | A1* | 4/2009 | Glimsdale | A61B 17/12172 623/1.35 |
| 2009/0112249 | A1* | 4/2009 | Miles | A61B 17/12122 606/192 |
| 2009/0171386 | A1* | 7/2009 | Amplatz | A61B 17/0057 606/213 |
| 2010/0211046 | A1* | 8/2010 | Adams | A61B 17/0057 604/524 |
| 2011/0054515 | A1 | 3/2011 | Bridgeman et al. | |
| 2012/0065667 | A1* | 3/2012 | Javois | A61B 17/12122 606/213 |
| 2012/0172927 | A1* | 7/2012 | Campbell | A61B 17/0057 606/213 |
| 2012/0271337 | A1* | 10/2012 | Figulla | A61B 17/0057 606/191 |
| 2012/0283585 | A1* | 11/2012 | Werneth | A61B 17/0057 600/508 |
| 2012/0323267 | A1* | 12/2012 | Ren | A61B 17/12172 606/191 |
| 2013/0006343 | A1* | 1/2013 | Kassab | A61B 17/12172 623/1.11 |
| 2013/0131717 | A1* | 5/2013 | Glimsdale | A61B 17/12122 606/213 |
| 2013/0178886 | A1* | 7/2013 | Liu | A61B 17/0057 606/198 |
| 2013/0218192 | A1* | 8/2013 | Erzberger | A61B 17/12122 606/200 |
| 2013/0296912 | A1* | 11/2013 | Ottma | A61B 17/0057 606/191 |
| 2014/0135817 | A1* | 5/2014 | Tischler | A61B 17/0057 606/200 |
| 2014/0142612 | A1* | 5/2014 | Li | A61B 17/12122 606/200 |
| 2014/0155932 | A1* | 6/2014 | Weishaupt | A61B 17/12109 606/200 |
| 2014/0172005 | A1* | 6/2014 | De Cannier | A61B 17/1214 606/200 |
| 2015/0005810 | A1* | 1/2015 | Center | A61B 17/12177 606/200 |
| 2015/0250482 | A1* | 9/2015 | Slaughter | A61B 17/12122 606/200 |
| 2015/0342612 | A1* | 12/2015 | Wu | A61B 17/12031 606/200 |
| 2016/0249898 | A1* | 9/2016 | Widmer | A61B 17/0057 606/213 |
| 2017/0035433 | A1* | 2/2017 | Forbes | A61B 17/12122 |
| 2017/0156898 | A1* | 6/2017 | Obradovic | A61B 17/12122 |
| 2017/0340336 | A1* | 11/2017 | Osypka | A61B 17/12122 |

FOREIGN PATENT DOCUMENTS

| | | |
|---|---|---|
| CN | 104352260 A | 2/2015 |
| WO | 2007/035497 A1 | 3/2007 |

OTHER PUBLICATIONS

Office Action dated Dec. 27, 2017 of corresponding Chinese Application No. 201511033727.0; 4 pgs.

* cited by examiner

LEFT ATRIAL APPENDAGE OCCLUDER

FIELD

The present disclosure relates to a medical device, and more particularly relates to a left atrial appendage occluder.

BACKGROUND

At present, an occluder may be put into a left atrial appendage through a catheter intervention method to prevent a thrombus formed in the left atrial appendage due to atrial fibrillation and avoid apoplexy caused by a fact that the thrombus goes up to a brain, or prevent systematic embolism caused by a fact that the thrombus reaches other portions of a body through the body's blood circulation system. Such left atrial appendage occluders substantially include an integrated occluder and a split occluder according to their structures. For example, the split occluder generally includes a fixing component and a sealing component which are connected with each other; the fixing component is disposed in a cavity of the left atrial appendage to fix the whole occluder; and the sealing component seals an opening portion of the left atrial appendage to prevent blood flow from flowing into the cavity of the left atrial appendage.

For the split occluder of this type, the fixing component is generally arranged in the cavity of the left atrial appendage by means of an anchor, and the anchor punctures the wall of the left atrial appendage to fix the fixing component in the cavity of the left atrial appendage. To reduce a risk that the occluder falls off, the fixing component is generally arranged at a deeper part of the cavity of the left atrial appendage. However, the deeper part of the cavity of the left atrial appendage is also a thinner part of the wall of the left atrial appendage, so that the fixing component will easily pierce the wall of the left atrial appendage, which will cause pericardial effusion, pericardial tamponade and other adverse consequences.

SUMMARY

In view of the above-mentioned problems, it is necessary to provide a left atrial appendage occluder, which can not only guarantee a stable fixing effect but also reduce the risk of piercing the wall of a left atrial appendage.

A technical scheme adopted to solve the technical problems is as follows: a left atrial appendage occluder is provided, including a sealing plate, a fixing frame located on one side of the sealing plate, and a connection member for connecting the sealing plate with the fixing frame. The fixing frame includes a first fixing connector, a second fixing connector and a plurality of supporting rods; the first ends of the multiple supporting rods are gathered and fixed by the first fixing connector; the second ends of the supporting rods are gathered and fixed by the second fixing connector; and the connection member is connected with the first fixing connector.

In one embodiment, the radial deformability of the sealing plate is greater than that of the fixing frame, and/or the axial deformability of the sealing plate is greater than that of the fixing frame.

In one embodiment, under the action of the same radial force, a radial length variation of the sealing plate is greater than that of the fixing frame; or under the action of the same radial force, a radial length change rate of the sealing plate is greater than that of the fixing frame; or, under the action of the same axial force, a displacement of the sealing plate along an axial force direction is greater than that of the fixing frame along the axial force direction.

In one embodiment, each supporting rod includes a proximal supporting section, a distal supporting section and a middle supporting section connected between the proximal supporting section and the distal supporting section; in a naturally unfolded state of the fixing frame, the middle supporting sections of the supporting rods are arrayed in a spacing manner along a circumferential direction, and cooperate with one another to form a columnar space in an encircling manner; one end of each proximal supporting section is connected with one end of each middle supporting section, and the other end of the proximal supporting section is connected with the first fixing connector; and one end of each distal supporting section is connected with each middle supporting section, and the other end of the distal supporting section is connected with the second fixing connector.

In one embodiment, the length of the middle supporting sections is in a range from 3 mm to 30 mm.

In one embodiment, an included angle between the middle supporting section and the distal supporting section is in a range from 15 degrees to 90 degrees or 90 degrees to 165 degrees.

In one embodiment, the left atrial appendage occlude further includes anchor bars arranged on the middle supporting sections and facing to the sealing plate.

In one embodiment, the left atrial appendage occluder further includes a film at least covering the middle supporting sections.

In one embodiment, the middle supporting sections are basically or substantially parallel to the central longitudinal axis of the fixing frame.

In one embodiment, the connection member is a flexible connection member or an elastic connection member.

In one embodiment, the connection member includes a proximal connecting end, a distal connecting end and a connection body connected between the proximal connecting end and the distal connection end; the proximal connecting end is connected with the sealing plate; the distal connecting end is connected with the fixing frame; the distal connecting end includes a ball socket; and the distal end of the connection body includes a ball head matched with the ball socket.

In one embodiment, the connection body is an elastic or flexible rod element or is of a spring structure or a woven structure.

In one embodiment, the sealing plate is of a double filament woven structure.

In one embodiment, the number of the supporting rods is in a range from 2 to 6 supporting rods.

In one embodiment, the distal end of the second fixing connector of the fixing frame is a spherical structure.

In one embodiment, the film covers the whole outer surface of the middle supporting sections.

In one embodiment, the connecting rod is a rod structure with a diameter of 0.1 mm to 5 mm.

In one embodiment, the ball head and the ball socket form a hinge mechanism.

In one embodiment, the ball head includes a convex spherical surface facing to the ball socket, the ball socket includes a concave spherical surface facing to the ball head; the convex spherical surface is contained in the concave spherical surface to form a moveable connection.

In one embodiment, the ball head and the ball socket can rotate at any angle.

In the left atrial appendage occluder of the present disclosure, the fixing frame is of a structure, which includes at least two supporting rods and has two closed ends, so that a contact area of the outer surface of the fixing frame and a left atrial appendage may be enlarged. When placed at a proper position in the left atrial appendage, the fixing frame may be compressed, and its supporting rods may provide a relatively high supporting force to the left atrial appendage to guarantee stable fixing, so that the fixing frame may be stably fixed in the left atrial appendage without the anchor bars, and an injury to a cavity wall of the left atrial appendage may be avoided.

Further, the anchor bars arranged on the fixing frame may puncture the wall of the left atrial appendage conveniently, which is helpful to fix the left atrial appendage occluder. A film attached to the fixing frame may prevent such a phenomenon that blood flows into the pericardium due to the fact that the anchor bars pierce the wall of the left atrial appendage. This film is a second seal between the left atrial appendage and the left atrium as well to prevent a circulation between the left atrial appendage and the left atrium.

In addition, the sealing plate is a disk shape woven by multiple metal wires and has good elasticity or elastic properties. The sealing plate is arranged at an opening portion of the left atrial appendage and may be well fitted to the opening portion of the left atrial appendage to achieve the best sealing effect. A thread is formed at the proximal end of the sealing plate to realize connection with a deliverer.

Further, the connection member is elastic and relatively high in bending resistance, so that a length and an angle between the sealing plate and the fixing frame may be adjusted; and in a situation where the sealing plate and the fixing frame are not coaxial, and it is required by the anatomical structure of the left atrial appendage, the length and the angle between the sealing plate and the fixing frame may be adjusted, so that the stable fixing effect is guaranteed, and the optimal sealing effect may be achieved.

DETAILED DESCRIPTION

For the purpose of making the description of a structure of a left atrial appendage occluder clearer, the present disclosure defines terms "distal end" and "proximal end". The above-mentioned terms are common used in the field of interventional medical devices. To be more specific, the "distal end" represents an end far away from an operator in a surgical process, and the "proximal end" represents an end close to the operator in the surgical process.

Figure 1:
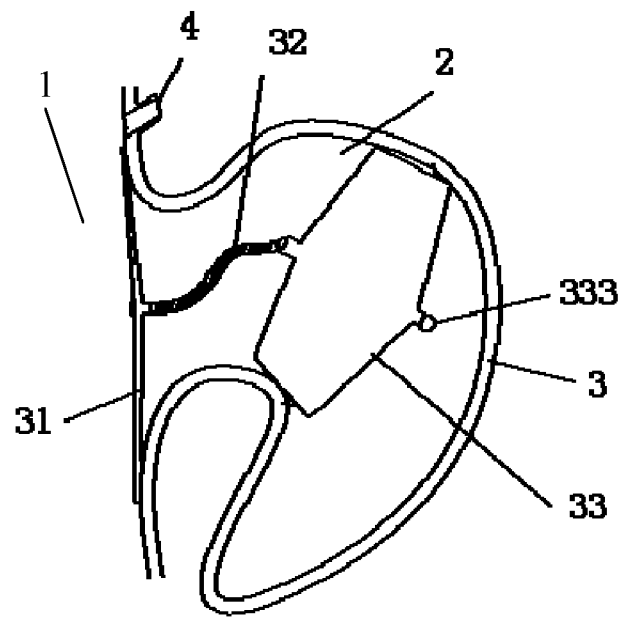
FIG. 1 is a schematic diagram of a state of a left atrial appendage occluder provided by one embodiment of the present disclosure after the left atrial appendage occluder has been implanted.
Figure 2:
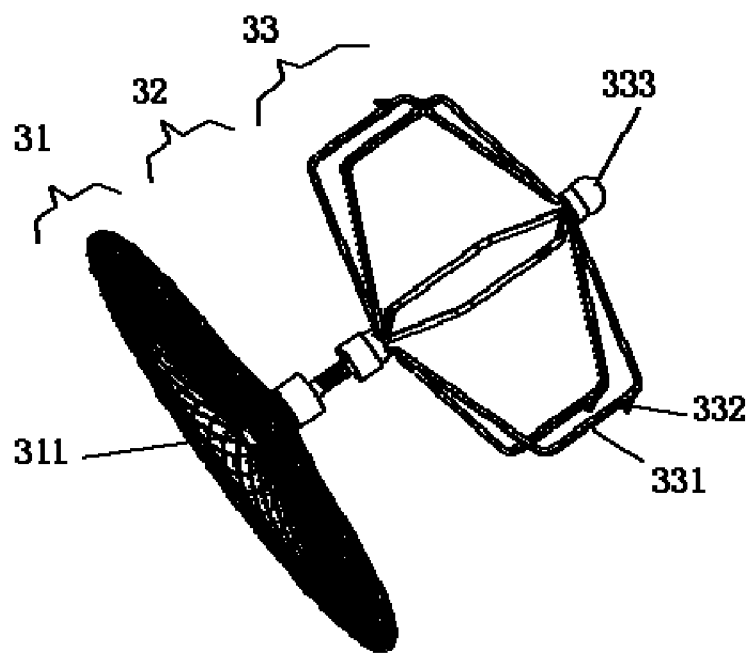
FIG. 2 is a schematic diagram of a left atrial appendage occluder provided by one embodiment of the present disclosure.

FIG. 1 illustrates a schematic diagram of a left atrial appendage occluder implanted into a left atrial appendage according to an embodiment of the present disclosure. The left atrial appendage 2 is located inside a left atrium 1 and between a mitral valve (not shown in figures) and a left superior pulmonary vein 4. With reference to FIG. 2 at the same time, the left atrial appendage occluder includes a sealing plate 31, a fixing frame 33 located on one side of the distal end of the sealing plate 31, and a connection member 32 for connecting the sealing plate 31 with the fixing frame 33.

Figure 3:
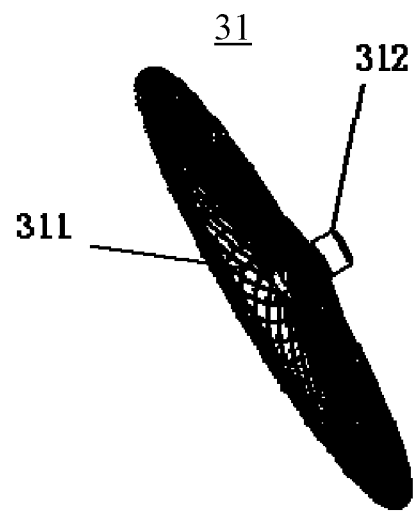
FIG. 3 is a schematic diagram of a sealing plate of the left atrial appendage occluder in FIG. 2.

With reference to FIG. 3 at the same time, the sealing plate 31 is of a filament woven structure, for example, it may be of a double-layer filament woven structure. The sealing plate 31 may be formed by weaving metal wires (a nickel-titanium material is preferred), and then by a heat treatment. The number of the metal wires is 16 to 144, and before example 36 to 72, and the diameter of each metal wire is 0.01 mm to 0.8 mm. The sealing plate 31 is substantially in a disk shape, and its diameter is greater than the maximum diameter of an opening portion of the left atrial appendage 2. The sealing plate 31 may adapt to left atrial appendages 2 with various opening shapes as long as the specification of the sealing plate 31 selected is large enough to cover the opening portion of each left atrial appendage 2. The sealing plate 31 is arranged at the opening portion of the left atrial appendage 2 and seals the opening portion, which can prevent a flow channel built between the left atrial appendage 2 and the left atrium 1 and can prevent blood from entering the left atrial appendage 1.

Proximal ends of the metal wires of the sealing plate 31 are gathered and fixed by a proximal fixing member 311, and distal ends of the metal wires of the sealing plate 31 are gathered and fixed by a distal fixing member 312. The proximal fixing member 311 and the sealing plate 31 can be fixed in a conventional way such as welding, as well as the distal fixing member 312 and the metal wires of the sealing plate 31. The distal fixing member 312 is connected with the connection member 32. Further, the proximal fixing member 311 has threads, and the threads may be connected with a deliverer to deliver the left atrial appendage occluder.

Figure 4:
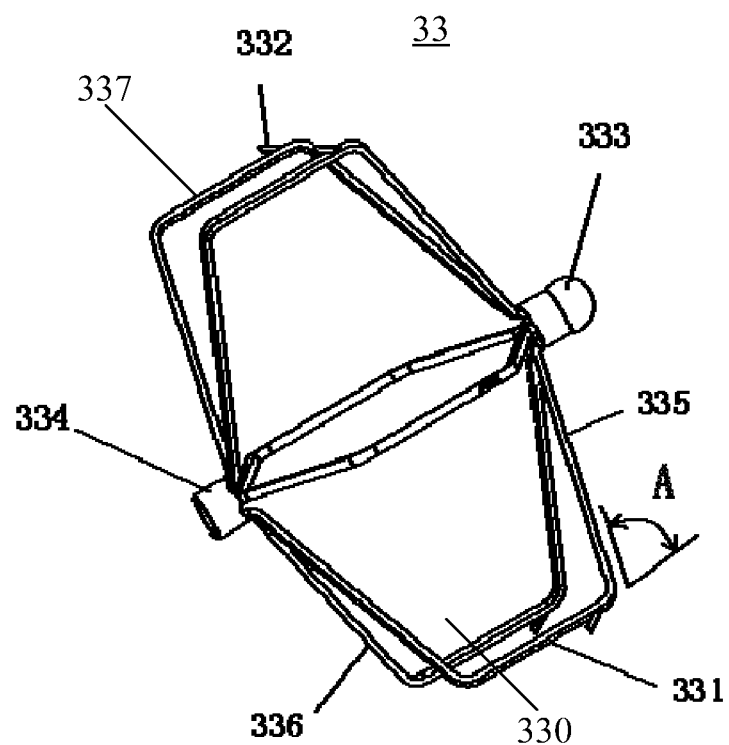
FIG. 4 is a schematic diagram of a fixing frame of the left atrial appendage occluder in FIG. 2.

Further, the interior of the sealing plate 31 is provided with a sealing film (not shown in figures), and the size of the sealing film is basically the same as that of the sealing plate 31. To be more specific, the diameter of the sealing film is equal to that of the sealing plate 31. The sealing film is made of a polymer material, preferably PTFE (polytetrafluoroethylene) or PET (polyethylene terephthalate). The sealing film may be fixed with the metal wires, which constitute the sealing plate 31, by sewing or gluing. With reference to FIG. 4, in one embodiment, the fixing frame 33 includes a first fixing connector 334, a second fixing connector 333 and multiple supporting rods 331. The first fixing connector 334 is located at the proximal end of the fixing frame 33; first ends of the multiple supporting rods 331, namely proximal ends of the supporting rods 331, are received and fixed by the first fixing connector 334; and second ends of the multiple supporting rods 331, namely distal ends of the supporting rods 331, are received and fixed by the second fixing connector 333. The first fixing connector 334 is connected with the connection member 32.

By optimizing the structure of the fixing frame of the left atrial appendage occluder of the present disclosure and making two ends of the fixing frame in closed states, so that the contact area between the outer surface of the fixing frame and the left atrial appendage 1 may be enlarged. As shown in FIG. 1, the fixing frame 33 is compressed by a cavity wall 3 of the left atrial appendage 2, and then is attached to the cavity wall 3 effectively by friction force between the cavity wall 3 and the fixing frame 33. Because the two ends of the fixing frame 33 are closed, the fixing frame 33 still may provide a sufficient supporting force when it is compressed and deformed so as to ensure that the left atrial appendage occluder may be stably fixed in the left atrial appendage 1. Further, the above structural features of the fixing frame allow the fixing frame to be stably fixed in the left atrial appendage 2 without anchor bars. Because of the smooth surface of the fixing frame, the fixing frame will not pierce the cavity wall 3 of the left atrial appendage 2 even if the fixing frame is arranged at a deeper position (where the cavity wall 3 is thinner) of the left atrial appendage 2.

With reference to FIG. 4, each supporting rod 331 includes a proximal supporting rod (also called a proximal supporting section) 336, a distal supporting rod (also called a distal supporting section) 335, and a middle supporting rod (also called a middle supporting section) 337 connected between the proximal supporting rod 336 and the distal supporting rod 335. When the fixing frame 33 is in a naturally unfolded state, the middle supporting rods 337 of the multiple supporting rods 331 are spaced to form a columnar space 330 in an encircling manner. Each proximal supporting rod 336 bends from one end of each middle supporting rod 337, and then connects to the first fixing connector 334 located at the axial line of the columnar space 330. And each distal supporting rod 335 bends from another end of the middle supporting rod 337 and then connects to the second fixing connector 333 located at the axial line of the columnar space 330.

The number of supporting rods 331 is not less than 2, and can preferably number six. The length of middle supporting rods is 3 mm to 30 mm, and this length may ensure that there are enough sufficient contact points and contact area between the fixing frame 33 and the cavity wall 3 of the left atrial appendage 2 to guarantee the connection is stable. In some embodiments, an anchor bar 332 is arranged on the middle supporting rod 337. The anchor bar 332 may face to the sealing plate. The anchor bar 332 is used for puncturing the cavity wall 3 of the left atrial appendage 2 to assist the fixing frame 33 in fixing. It can be understood that the fixing frame 33 can firmly attached to the cavity wall 3 of the left atrial appendage 2 due to the closed structure of the fixing frame 33 at both ends, the anchor bar 332 on the fixing frame 33 may be also omitted in some embodiments to avoid piercing the cavity wall 3 of the left atrial appendage 2.

Figure 5:
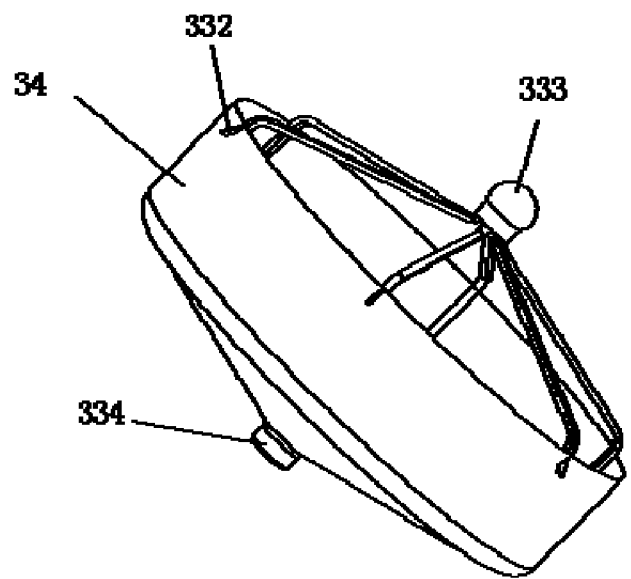
FIG. 5 is a schematic diagram of a fixing frame of a left atrial appendage occluder provided by another embodiment of the present disclosure.

With reference to FIG. 5, in some other embodiments, the fixing frame 33 also may include a film 34. The film 34 at least covers a part, which has the anchor bars 332, of the fixing frame 33. The film 34 also may cover the whole outer surface of the fixing frame 33. When the specification is improper, the film 34 arranged on the outer surface of the fixing frame 33 may prevent a phenomenon where blood flows into the pericardium due to the fact that the anchor bars 332 pierce the cavity wall 3 of the left atrial appendage 2. Meanwhile, the film 34 is also a second seal between the left atrial appendage 2 and the left atrium 1 to prevent a circulation between the left atrial appendage 2 and the left atrium 1. The film 34 is made of a polymer material which may be the PTFE or the PET. The film 34 may be attached to the fixing frame 33 by swing or gluing.

The distal end of the second fixing connector 333 of the fixing frame 33 is spherical. And the spherical structure at the distal end of the fixing frame 33 can avoid sharp edges, so as to prevent the left atrial appendage occluder damaging the left atrial appendage 2.

The fixing frame 33 may be formed by heat treatment after cutting a metal tube. To be more specific, the fixing frame 33 may be formed by cutting a metal (preferably a nickel-titanium material) tube with a diameter of 0.3 mm to 5 mm into a certain pattern, and then shaped by heat treatment. The first fixing connector 334 and the second fixing connector 333 are both integrated with the supporting rods 331. The spherical structure of the second fixing connector 333 may be formed by melting part of the material of the metal tube through laser or argon arc welding.

In some other embodiments, the fixing frame 33 also may be formed by connecting multiple metal wires after these metal wires had been heat treated. For example, the fixing frame 33 may be formed by connecting multiple metal wires with diameters of 0.05 mm to 0.8 mm or flat metal wires with sectional areas of (0.03 mm to 0.5 mm)×(0.5 mm to 0.03 mm) after these metal wires had been heat treated, and the metal is preferably nickel-titanium. The distal ends and the proximal ends of the metal wires may be fixed by welding to form the first fixing connector 334 and the second fixing connector 333. The spherical structure of the second fixing connector 33 also may be formed by melting part of the material of the metal tube through laser or argon arc welding.

Figure 6:
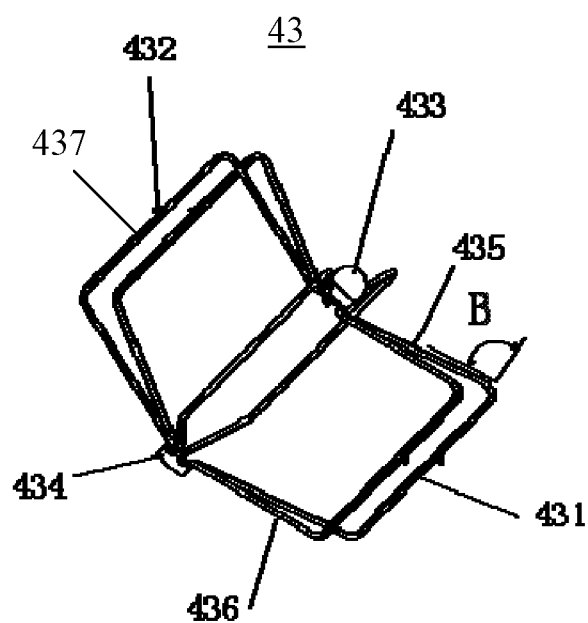
FIG. 6 is a schematic diagram of a fixing frame of a left atrial appendage occluder provided by another embodiment of the present disclosure.

As shown in FIG. 4, an included angle A between the middle supporting rod 337 and the distal supporting rods 335 is 90 degrees to 165 degrees. This included angle enables each distal supporting rod 335 to convexly extend from the corresponding end of each middle supporting rod 337 towards the distal end. The multiple distal supporting rods 335 form a conical surface which protrudes towards the distal end and has a vertex located outside the columnar space 330. This design of the included angle may enable the distal supporting rods 335 to resist more dramatic deformation of the middle supporting rods 337 so as to guarantee the sufficient supporting force. The same included angle A is also formed between the middle supporting rod 337 and the proximal supporting rod 336. As shown in FIG. 6, in some other embodiments, a fixing frame 43 is of a structure similar to that of the fixing frame 33 as shown in FIG. 4, but their shapes are slightly different. To be more specific, this fixing frame 43 also has a first fixing connector 434, a second fixing connector 433 and multiple supporting rods 431 connected between the first fixing connector 434 and a second fixing connector 433. Each supporting rod 431 also includes a proximal supporting rod 436, a distal supporting rod 435 and a middle supporting rod 437 connected between the proximal supporting rod 436 and the distal supporting rod 435. Anchor bars 432 are arranged on the middle supporting rods 437. The distal end of the second fixing connector 433 is of a spherical structure. What is different is that an included angle B between the middle supporting rod 437 and the distal supporting rod 435 is between 15 degrees and 90 degrees, so that all the distal supporting rods 435 form a conical surface sunken towards the proximal end in an encircling manner. After the left atrial appendage occluder has been implanted into the left atrial appendage 2, a phenomenon, that the distal end of the fixing frame 43 protrudes and pierces the left atrial appendage 2 when the fixing frame 43 is compressed, will be avoided due to these included angles. In addition, on the basis of guaranteeing the original stable performance, the length of the fixing frame 43 will be greatly reduced after the left atrial appendage occluder has been implanted into the left atrial appendage 2, so that the left atrial appendage occluder may adapt to a left atrial appendage 2 with a shallow cavity and be suitable for more types of left atrial appendages 2.

An included angle B, formed between the proximal supporting rod 436 and the middle supporting rods 437, has the same size with included angle A.

Figure 7:
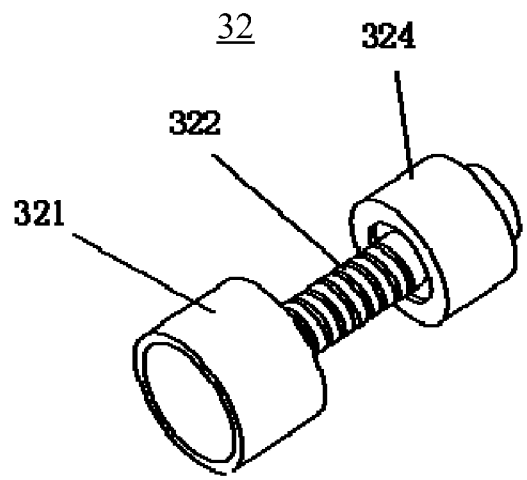
FIG. 7 is a schematic diagram of a connection member of the left atrial appendage occluder in FIG. 2.
Figure 8:
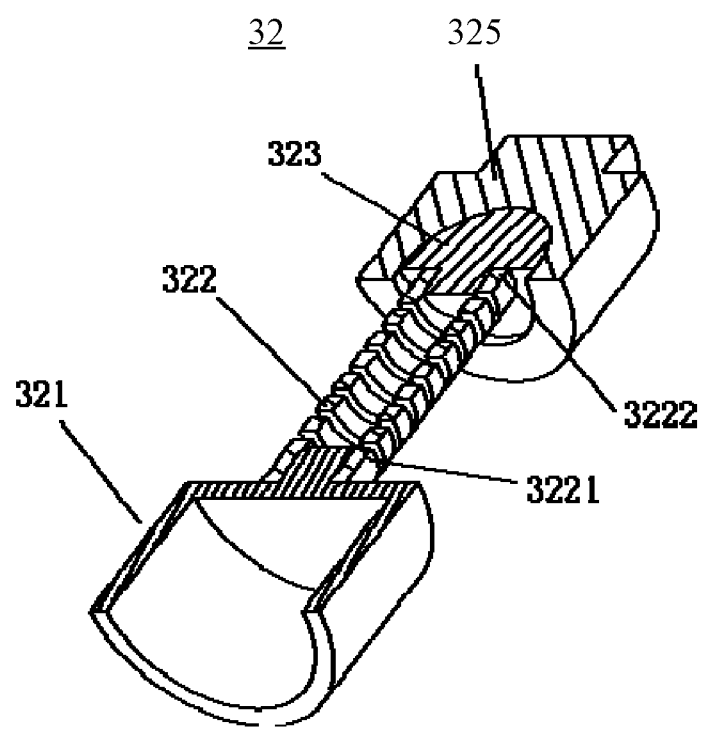
FIG. 8 is a section view of the connection member in FIG. 7.

With reference to FIG. 7 and FIG. 8, the connection member 32 includes a proximal connecting end 321, a distal connecting end 324 and a connecting rod 322 connected between the proximal connecting end 321 and the distal connecting end 324.

The proximal connecting end 321 is connected with the sealing plate 31. To be more specific, the proximal connecting end 321 is connected with the distal fixing member 312 of the sealing plate 31. The connection may be realized by welding, adhering, or of interference fit or other ways.

The distal connecting end 324 is connected with the fixing frame 33. To be more specific, the distal connecting end 324 is connected with the first fixing connector 334 of the fixing frame 33. The connection may be realized by welding, adhering, or of interference fit or other ways.

The distal connecting end 324 includes a ball head structure 323 and a ball socket structure 325 which are matched with each other. A hinge mechanism, formed by the ball head structure 323 and the ball socket structure 325, may adjust an angle within 360 degrees. The ball head structure 323 is connected with the connecting rod 322, and the ball socket structure 325 is connected with the fixing frame 33, so that an angle between the fixing frame 33 and the connection member 32 also may be flexibly adjusted, and the left atrial appendage occluder may adapt to left atrial appendages 2 with different shapes in a wider range.

Figure 9:
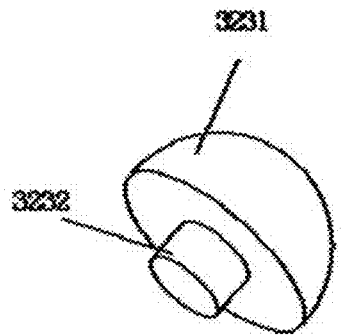
FIG. 9 is a schematic diagram of a portion in the distal end of the connection member in FIG. 7.
Figure 10:
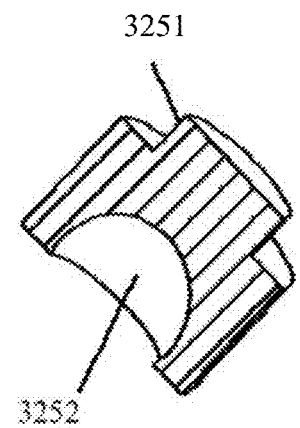
FIG. 10 is a schematic diagram of another portion in the distal end of the connection member in FIG. 7.

With reference to FIG. 8, FIG. 9 and FIG. 10 at the same time, the proximal connecting end 321 is connected with the proximal end 3221 of the connecting rod 322 by welding, adhering, or of interference fit or other ways. The ball head structure 323 includes a convex spherical surface 3231 facing to the ball socket structure 325, and a convex pillar 3232 facing to the connecting rod 322. The ball socket structure 325 includes a convex end 3251 facing to the fixing frame 33 and a concave spherical surface 3252 facing to the ball head structure 323. The distal end 3222 of the connecting rod 322 is connected with the convex pillar 3232 of the ball head structure 323 by welding, adhering, or of interference fit, or other ways. The convex end 3251 of the ball socket structure 325 is connected with the first fixing connector 334 of the fixing frame 33. The convex spherical surface 3231 is contained in the concave spherical surface 3252 to form a movable connection, so that the ball socket structure 325 and the ball head structure 323 may rotate at any angle.

The connection member 32 may be made of a metal with better biocompatibility, such as stainless steel or a nickel-titanium material. The connecting rod 322 may be of a rod structure with a diameter of 0.1 mm to 5 mm, and also may be a spring structure. Therefore, it can not only change a connection angle between the connection member 32 and the fixing frame 33, but also adjust the length of the connection member 32, so that the left atrial appendage occluder may adapt to more left atrial appendages with different shapes, and its own movements of the left atrial appendage after the left atrial appendage occluder has been implanted into the left atrial appendage.

As shown in FIG. 1, after the left atrial appendage occluder is implanted into a left atrial appendage 2 with a large bending angle, the fixing frame 33 needs to find a proper fixing position in the left atrial appendage 2, but there is a relatively large included angle between this fixing position and the opening portion of the left atrial appendage 2, that is, after the left atrial appendage occluder is implanted into the left atrial appendage 2, a relatively large included angle and long distance are formed between the fixing frame 33 and the sealing plate 31. And by adjusting the length and the angle of the connection member 32, it is able to adjust the included angle and the relative distance which are formed between the fixing frame 33 and the sealing plate 31, so that the fixing frame 33 of the left atrial appendage occluder can be stably fixed at a proper position in the left atrial appendage 2, and the sealing plate 31 may be optimally fitted to the opening portion of the left atrial appendage 2 to achieve sealing.

In one specific embodiment of the present disclosure, the deformability of the sealing plate 31 is greater than that of the fixing frame 33. The deformability of a certain component or structure is the magnitude of a deformation of this component or structure under the action of an external force. In this present disclosure, the deformability described herein may be expressed by a radial length (for example the diameter) variation of the component or structure under the action of a radial force.

Further, the radial deformability of the sealing plate 31 of the left atrial appendage occluder is greater than that of the fixing frame 33, and/or the axial deformability of the sealing plate 31 is greater than that of the fixing frame 33. To be more specific, under the action of the same radial force, the radial length variation of the sealing plate 31 is greater than that of the fixing frame 33; or under the action of the same radial force, a radial length change rate of the sealing plate 31 is greater than that of the fixing frame 33; or under the action of the same axial force, a displacement of the sealing plate 31 along an axial force direction is greater than that of the fixing frame.

Radial length changes of the fixing frame and the sealing plate under the action of the same radial force may be respectively tested by adopting a flat plate method. For example, with reference to FIG. 11 and FIG. 12, the left atrial appendage occluder may be tested by the flat plate method.

Figure 11:
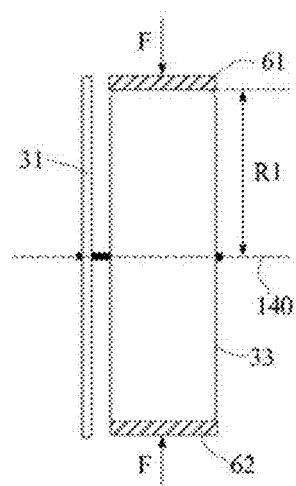
FIG. 11 is a schematic diagram of a test method of the radial deformability of the fixing frame of the left atrial appendage occluder in FIG. 2.

With reference to FIG. 11, firstly, on the premise that the sealing plate 31 maintains a freely unfolded state, radial acting forces F are applied to the fixing frame 33 by two parallel flat plates 61 and 62. To be more specific, the parallel flat plates 61 and 62 are respectively placed on two opposite sides of a diameter of the fixing frame 33, and two radial acting forces F with the same sizes and opposite directions are respectively applied to the flat plates 61 and 62 along the diameter. The diameter of the fixing frame 33 penetrates through and is perpendicular to a central axial line 140. The two parallel flat plates 61 and 62 maintain a mutually parallel state in the whole test process, namely the flat plates are parallel to the central axial line 140 all the time in the test process. And any one of the flat plates at least covers a contour with maximum radius (for example, the middle supporting rods/sections) of the fixing frame 33, and preferably the flat plate covers the whole fixing frame 33 in a direction parallel to the central axial line 140. In the naturally unfolded state, the radial lengths of portions, where the flat plates are loaded, of the fixing frame 33 are R1, the radial length variation of the fixing frame 33, under the action of the radial forces F, is a radial length difference obtained before and after radial compression, and may be expressed by $\Delta R1$, so that the radial length change rate is $\Delta R1/R1$. In order to guarantee that the flat plate itself is not deformed in a radial force applying process, and the radial forces can be evenly applied to all portions of the flat plates, a thickness of the flat plates is at least 5 mm.

Figure 12:
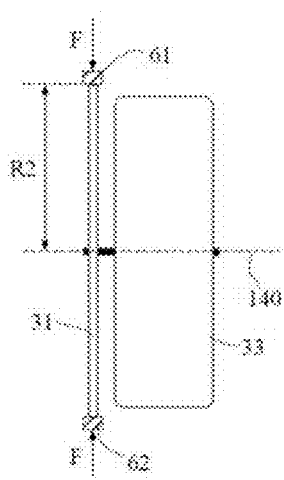
FIG. 12 is a schematic diagram of a test method of the radial deformability of the sealing plate of the left atrial appendage occluder in FIG. 2.

With reference to FIG. 12, the sealing plate 31 is tested by the flat plate method as above, namely the same radial acting forces F which refer to the same size, direction and acting time, are adopted. On the premise that the sealing plate 31 is naturally unfolded, the radial length variation $\Delta R2$ or the radial length change rate $\Delta R2/R2$ of the sealing plate 31 is tested; and, at the moment, a contour with maximum radius of the sealing plate 31 is located at the edges of the double plates. Based on the above test condition, under the action of the same radial force, the radial length variation $\Delta R2$ of the sealing plate 31 of the left atrial appendage occluder according to the embodiment of the present disclosure is greater than the radial length variation $\Delta R1$ of the fixing frame 33; or the radial length change rate $\Delta R2/R2$ of the sealing plate 31 of the left atrial appendage occluder according to the embodiment of the present disclosure is greater than the radial length change rate $\Delta R1/R1$ of the fixing frame 33.

After the left atrial appendage occluder is implanted into a human body, a situation that the implantation location may be improperly selected may occur. For example, if the fixing frame extends too deep into the cavity of the left atrial appendage, an axial length of the occluder in the naturally unfolded state would be shorter than a relative distance between the fixing frame and the sealing plate after implantation, which will lead to a mutual traction between the fixing frame and the sealing plate. Or, the implanted occluder would move together with the heart, and the implanted occluder and the heart have different amplitudes or directions of motion, which may lead to the mutual traction between the fixing frame and the sealing plate. Generally, the fixing plate and the sealing plate pull each other through the connection member.

When the fixing frame is pulled by the sealing plate, as the fixing frame is fixed in the cavity of the left atrial appendage through a radial supporting force surrounding a circumferential region of the central axial line 140, the fixing frame is attached to the circumferential region of the cavity of the left atrial appendage to resist this pulling acting force. Therefore, the fixing frame will be radially deformed under the axial acting force, and the fixing frame will separate from the cavity wall of the left atrial appendage if the acting force is large enough, and then the left atrial appendage occluder would fall off, which will cause an implantation failure. When the sealing plate is pulled by the fixing frame, the sealing plate has a disk surface structure and is connected with the connection member through the disk surface, so that the axial pulling on the sealing plate would also lead to a radial deformation of the sealing plate.

Therefore, when the fixing frame and the sealing plate pull each other, the one who is easily deformed in the radial direction will be pulled by the other one. For example, under the same radial acting force, as the radial length variation of the fixing frame according to the embodiment of the present disclosure is less than that of the sealing plate, or the radial length change rate of the fixing frame according to the embodiment of the present disclosure is less than that of the sealing plate, in the mutual traction, the fixing frame would dominate the traction and pull the sealing plate to make the sealing plate deform towards the fixing frame direction (or towards the distal end). Such deformation enables the sealing plate to be more close to a left atrial wall at an opening of the left atrial appendage than that of the sealing plate in the naturally unfolded state, which enhances a sealing effect between the sealing plate and the opening of the left atrial appendage and avoids an interval between the sealing plate and the left atrial wall, so that it can prevent apoplexy or systematic embolism caused by blood flowing into the cavity of the left atrial appendage and a thrombus flowing into a left atrium through the interval. In addition, the fixing frame dominates the traction so that the fixing frame will not easily separate from the cavity wall of the left atrial appendage under the pull of the sealing plate, and the occluder will be better fixed in the left atrial appendage to avoid falling off from the left atrial appendage.

Figure 13:
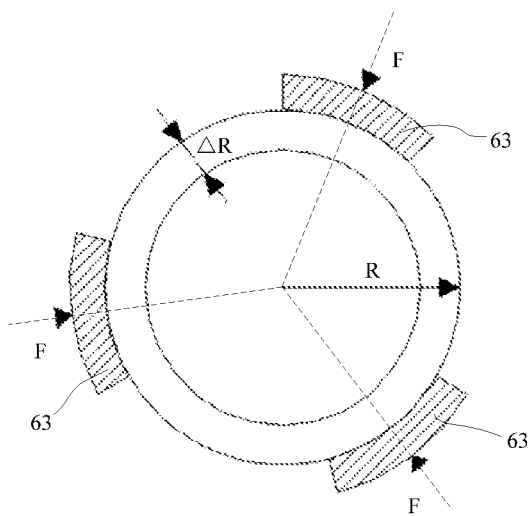
FIG. 13 is a schematic diagram of another specific test method of the radial deformability of the sealing plate/fixing frame of the left atrial appendage occluder in FIG. 2.

The above flat plate method is only an example method, and not a limitation of the present disclosure. An ordinary person skilled in the art can adopt any other proper method, equivalent to the flat plate method, for testing. For example, a test method that the radial acting force is evenly applied to a tested component in a circumferential direction. To be more specific, with reference to FIG. 13, three arc-shaped plates 63 may be uniformly disposed, in the same circumferential direction, on the contour with maximum radius of the tested component (the fixing frame or the sealing plate). During the test, radial acting forces F are simultaneously applied to the above arc-shaped plates 63 along a radial direction to test a variation or a change rate of a radial length R of the tested component. Similarly, in order to apply the radial force evenly, a thickness of the arc-shaped plates is at least 5 mm. Furthermore, the left atrial appendage occluder may be tested by a radial supporting force tester RX550-100 of the Machine Solution Inc. (MSI) Company.

In addition, when one portion of the tested component (the fixing frame or the sealing plate) is restricted, the axial deformability of the tested component is expressed by testing an axial displacement (along the direction of the central axial line 140) of the tested component under an action of the same axial force. In the test method as above, the above restriction is an equidimensional restriction, that is to say, in the restriction process, the tested component does not elastically deform or just deforms a little, which may be ignored basically. In addition, the axial acting force is applied to a position where no elastic deformation occurs, of the tested component. For example, the same axial acting forces are applied to end portions, which are connected with the connection member, of the tested component, and the axial displacement of the tested component is used to express its own deformability, and the axial displacement of the component here refers to a position of the tested component where the axial acting force is applied, and the left atrial appendage meets the condition that the axial displacement of the fixing frame is less than that of the sealing plate. During the testing, the fixing frame and the sealing plate are independently tested, for example, only a single fixing frame or a single sealing plate is tested at each time.

Figure 14:
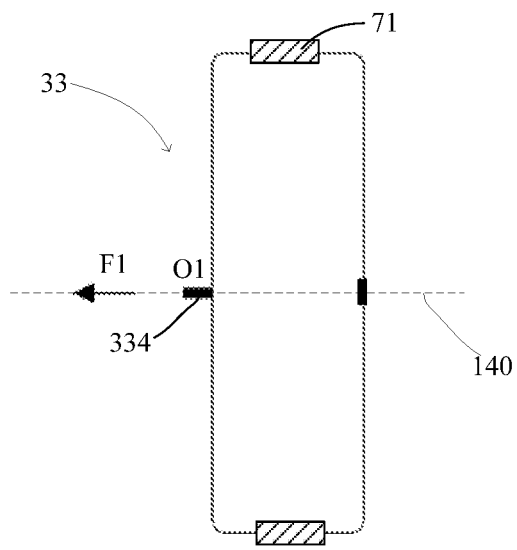
FIG. 14 is a schematic diagram of a first test method of the axial deformability of the fixing frame of the left atrial appendage occluder in FIG. 2.

With reference to FIG. 14, during a test of the fixing frame 33, a clamping portion, where the fixing frame 33 is clamped by an annular clamping member 71 along a circumferential direction, is the contour with maximum radius of the fixing frame 33. The annular clamping member 71 surrounds and is perpendicular to the central axial line 140. In a clamping process, the radial size of the clamping portion of the fixing frame 33 is basically equal to that of a fixing frame 33 in the naturally unfolded state, so that the elastic deformation may be ignored. An axial acting force F1, along the central axial 140 and towards the direction of the sealing plate 31, is applied to the first fixing connector 334, where the fixing frame 33 is connected with the connection member, and the first fixing connector 334 does not deform under the axial acting force F1. Measuring an axial displacement ΔO1 of a projection O1 of the first fixing connector 334 on the central axial line 140 under the F1. The axial displacement ΔO1 is used to express the deformation (or the deformability) of the fixing frame 33, and the state of the clamping member 71 itself maintains unchanged during the action of the axial acting force F1.

After the left atrial appendage occluder is implanted into the human body, and under a condition that one portion, such as the maximum contour, of the fixing frame is clamped, it can be seen that the tested axial displacement, under the action of the axial acting force, represents the axial deformability of the fixing frame, which is under the pull of the sealing plate and the restricting action of the cavity of the left atrial appendage. Under the same axial acting force, the larger the axial displacement ΔO1 is, the easier it is for the fixing frame to be pulled and deformed.

Figure 15:
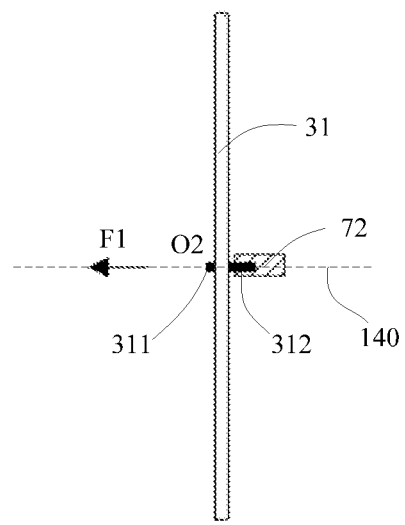
FIG. 15 is a schematic diagram of a first test method of the axial deformability of the sealing plate of the left atrial appendage occluder in FIG. 2.

With reference to FIG. 15, during a test of the sealing plate 31, the distal fixing member 312 of the sealing plate 31 is clamped by the clamping member 72 and the axial acting force F1, applied to the proximal fixing member 311 of the sealing plate 31 along the central axial line 140 and towards a direction away from the fixing frame 33, is equal to the test of the fixing frame 33. Measuring another axial displacement ΔO2 of a projection O2 of the proximal fixing member 311 on the central axial line 140 under the F1, and the axial displacement ΔO2 is used to express the deformation (or the deformability) of the sealing plate 31.

After the left atrial appendage occluder is implanted into the human body, and under a condition that one portion, such as the distal fixing member 312, of the sealing plate 31 is clamped, it can be seen that the tested axial displacement under the action of the axial acting force F1 represents the axial deformability of the sealing plate 31, which is under the pull of the fixing frame 33 and the restricting action of a tissue wall of the opening portion of the left atrial appendage. Under the same axial acting force, the larger the axial displacement ΔO2 is, the easier it is for the sealing plate 31 to be pulled and deformed.

It is tested that, under the action of the same axial force, the axial displacement ΔO1 of the fixing frame is less than the axial displacement ΔO2 of the sealing plate. It can be understood that when the fixing frame and the sealing plate pull each other, the one who has a larger axial displacement will be pulled by the other one. For example, under the same axial acting force, as the axial displacement of the fixing frame according to the embodiment of the present disclosure is less than that of the sealing plate, the fixing frame would dominate the traction and pull the sealing plate during the traction to make the sealing plate deform towards a direction of the fixing frame (or towards the distal end). Such deformation enables the sealing plate to be more close to the left atrial wall at the opening of the left atrial appendage than that of the sealing plate in the naturally unfolded state, which enhances a sealing effect between the sealing plate and the opening of the left atrial appendage and avoids an interval between the sealing plate and the left atrial wall, so that it can prevent blood from flowing into the cavity of the left atrial appendage and a thrombus from flowing into a left atrium through the interval. In addition, the fixing frame dominates the traction so that the fixing frame will not easily separate from the cavity wall of the left atrial appendage under the pull of the sealing plate, and the occluder will be better fixed in the left atrial appendage to avoid falling off from the left atrial appendage.

Figure 16:
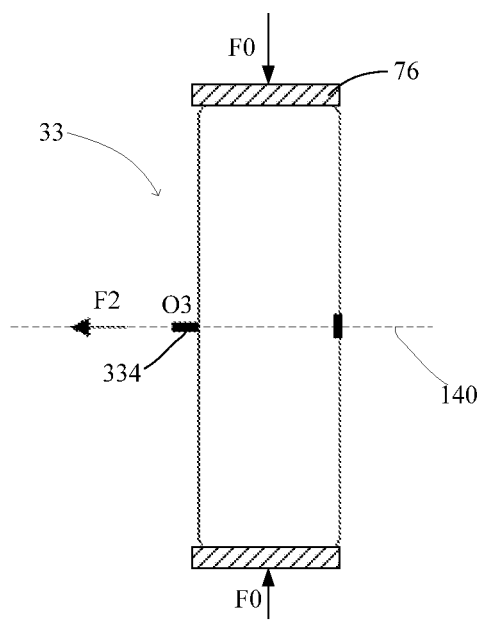
FIG. 16 is a schematic diagram of a second test method of the axial deformability of the fixing frame of the left atrial appendage occluder in FIG. 2.

A second axial deformability test method may be further adopted. With reference to FIG. 16, during a test of the fixing frame 33, a clamping portion, where the fixing frame 33 is clamped by an annular clamping member 76 along a circumferential direction, is a contour with maximum radius of the fixing frame 33. The annular clamping member surrounds, and is perpendicular, to the central axial line 140. In a clamping process, the radial size of the clamping portion of the fixing frame 33 is smaller than that of a fixing frame 33 in the naturally unfolded state. The clamping portion of the fixing frame 33 is compressed in the radial direction; for example, the maximum radial length after compression is 80 percent of the maximum radial length before it is compressed. Of course, other compression ratios may be adopted, which are not listed one by one here. For example, a radial force F0 may be applied to the annular clamping member 76 to compress the fixing frame 33 in the radial direction. An axial acting force F2 is applied to the end portion 330, where the fixing frame 33 is connected with the connection member, and the end portion 330 does not deform under the axial acting force F2, which is along the central axial line 140 and towards the direction of the sealing plate 31. A measurement of an axial displacement ΔO3 of a projection O3 of the end portion 330 on the central axial line 140 under the F2 can be made. The axial displacement ΔO3 is used to express the deformation (or the deformability) of the fixing frame 33.

After the left atrial appendage occluder is implanted into a human body, and under a condition that one portion, such as the maximum contour, of the fixing frame 33 is clamped, it can be seen that the tested axial displacement under the action of the axial acting force represents the deformability of the fixing frame 33, which is under the pull of the sealing plate 31 and the restricting action of the cavity of the left atrial appendage. Under the same axial acting force, the larger the axial displacement ΔO3 is, the easier it is for fixing frame 33 to be pulled and deformed.

Figure 17:
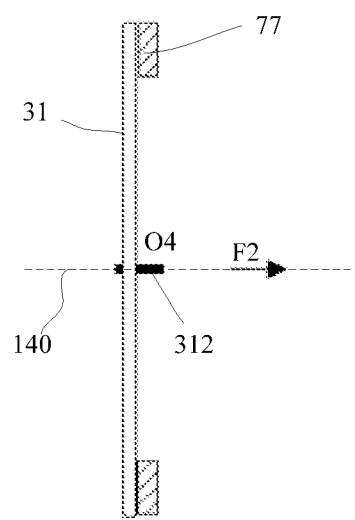
FIG. 17 is a schematic diagram of a second test method of the axial deformability of the sealing plate of the left atrial appendage occluder in FIG. 2.

With reference to FIG. 17, the sealing plate 31 includes a distal fixing member 312; and the connection member is connected with the distal fixing member 312. During an independent test of the sealing plate 31, an annular fixing member 77 abuts a disk surface, which is towards the fixing frame 33 and is located at the maximum edge of the sealing plate 31. Meanwhile, the axial acting force F2, along the central axial line 140 and towards a direction of the fixing frame 33, is applied to the distal fixing member 312. Under the axial acting force F2, a position where the disk surface is abutted maintains unchanged along the direction of the central axial line 140 due to the annular fixing member 77, thereby testing a projection displacement ΔO4 of the distal fixing member 312 on the central axial line 140.

It can be seen from the above that, after the left atrial appendage occluder is implanted into the human body, a portion of the sealing plate is blocked by the cavity wall of the left atrium at the opening portion of the left atrial appendage, wherein the portion of the sealing plate faces to the fixing frame and is at least the edge of the sealing plate with maximum radius. Therefore, during the above test of the sealing plate, and under a condition that the position, abutted by the annular fixing member 77, of the disk surface maintains unchanged along the direction of the central axial line 140, and an axial displacement, tested under the axial acting force, of the sealing plate represents the deformability of the sealing plate pulled by the fixing frame at the opening of the left atrial appendage after the occluder is implanted into the human body. Under the same axial acting force, the larger the axial displacement ΔO4 is, the easier the sealing plate will be pulled and deformed.

It is tested that, under the action of the same axial force (F2), the axial displacement ΔO3 of the fixing frame is less than the axial displacement ΔO4 of the sealing plate. It can be understood that when the fixing frame and the sealing plate pull each other, the one who has a larger axial displacement will be pulled by the other one. For example, under the same axial acting force, as the axial displacement of the fixing frame according to the embodiment of the present disclosure is less than that of the sealing plate, the fixing frame would dominate the traction and pull the sealing plate during the traction to make the sealing plate deform towards a direction of the fixing frame (or towards the distal end). Such deformation enables the sealing plate to closer to the left atrial wall at the opening portion of the left atrial appendage than that of the sealing plate in the naturally unfolded state, which enhances a sealing effect between the sealing plate and the opening of the left atrial appendage and avoids an interval between the sealing plate and the left atrial wall, so that it can prevent blood from flowing into the cavity of the left atrial appendage and a thrombus from flowing into a left atrium through the interval. In addition, the fixing frame dominates the traction so that the fixing frame will not easily separate from the cavity wall of the left atrial appendage under the pull of the sealing plate, and the occluder will be better fixed in the left atrial appendage to avoid falling off from the left atrial appendage.

Above all, the left atrial appendage occluder provided by the present disclosure has the following beneficial effects:

(1) the fixing frame is of the structure, which is formed of at least two supporting rods and has two closed ends, and the fixing frame is flexible and has a smooth outer surface. When placed at a proper position in the left atrial appendage, the fixing frame may be compressed, and its supporting rods may provide a relatively high supporting force to the left atrial appendage, to guarantee stable fixing, and may not injure the cavity wall of the left atrial appendage. The anchor bars further arranged on the fixing frame may puncture the wall of the left atrial appendage conveniently, which is helpful to fix the left atrial appendage occluder. The film attached to the fixing frame may prevent such a phenomenon that blood flows into the pericardium due to the fact that the anchor bars pierce the wall of the left atrial appendage. This film is a second seal between the left atrial appendage and the left atrium as well to prevent a circulation between the left atrial appendage and the left atrium.

(2) The sealing plate is a disk shape woven by multiple metal wires and has good elasticity or elastic properties. The sealing plate is arranged at the opening portion of the left atrial appendage and may be fitted to the opening portion of the left atrial appendage to achieve the best sealing effect. The thread is formed at the proximal end of the sealing plate to realize connection with a deliverer.

(3) The connection member has elasticity and relatively high bending resistance, so that it is able to adjust the length and the angle between the sealing plate and the fixing frame; and in a situation where the sealing plate and the fixing frame are not coaxial, and it is required by the anatomical structure of the left atrial appendage, the length and the angle between the sealing plate and the fixing frame may be adjusted, so that the stable fixing effect is guaranteed, and the optimal sealing effect may be achieved.

All technical features of the above embodiments may be randomly combined. In order to simplify the description, not all possible combinations of the respective technical features in the embodiments are described. However, the combinations of these technical features shall fall within the scope described in the description in case of no contradictions.

The above embodiments only express a few of embodiments of the present disclosure, and their descriptions are relatively specific and detailed, but shall not be regarded as limitations to the scope of the patent for the present disclosure. It should be noted that persons of ordinary skill in the art can further make a plurality of deformations and improvements without departing from the idea of the present disclosure, and these deformations and improvements shall all fall within the protection scope of the present disclosure. Therefore, the protection scope of the patent for the present disclosure shall be based on attached claims.

The invention claimed is:

1. A left atrial appendage occluder, comprising:
a sealing plate, a fixing frame located on one side of the sealing plate, and a connection member for connecting the sealing plate with the fixing frame, wherein the fixing frame comprises a central longitudinal axis along which a first fixing connector and a second fixing connector are aligned and a plurality of supporting rods of not less than 3 arranged around the central longitudinal axis, the supporting rods having first ends and second ends;
the first ends of the supporting rods are gathered and fixed by the first fixing connector; the second ends of the supporting rods are gathered and fixed by the second fixing connector; and
the connection member is connected with the first fixing connector;
wherein:
each supporting rod comprises a proximal supporting section, a distal supporting section, and a middle supporting section connected between the proximal supporting section and the distal supporting section, the middle supporting sections of the rods being substantially parallel to the central longitudinal axis of the fixing frame and having a length configured to ensure contact points and a contact area between the fixing frame and a cavity wall when placed in a left atrial appendage to create a stable connection;
anchor bars are arranged on the middle supporting sections and facing to the sealing plate, the anchors bars configured to puncture a wall in a left atrial appendage;

a film being positioned around the middle supporting sections along an outer diameter of the fixing frame and covering at least part of an outer surface of each middle supporting section;

in a naturally unfolded state of the fixing frame, the middle supporting sections of the supporting rods are arrayed in a spacing manner along a circumferential direction, and cooperate with one another to form a columnar space in an encircling manner about the central longitudinal axis;

one end of each proximal supporting section is connected with one end of each middle supporting section, and the other end of the proximal supporting section is connected with the first fixing connector;

one end of each distal supporting section is connected with each middle supporting section, and the other end of the distal supporting section is connected with the second fixing connector; and wherein the sealing plate and the fixing frame each have a radial deformability, and the radial deformability of the sealing plate is greater than that of the fixing frame such that under an action of a same radial force, a radial length variation of the sealing plate is greater than a radial length variation of the fixing frame or a radial length change rate of the sealing plate is greater than a radial length change rate of the fixing frame.

2. The left atrial appendage occluder according to claim 1, wherein the sealing plate and the fixing frame each have an axial deformability, and the axial deformability of the sealing plate is greater than that of the fixing frame.

3. The left atrial appendage occluder according to claim 2, wherein under an action of a same axial force, a displacement of the sealing plate along an axial force direction is greater than of the fixing frame along the axial force direction.

4. The left atrial appendage occluder according to claim 1, wherein the middle supporting sections have a length in a range from 3 mm to 30 mm.

5. The left atrial appendage occluder according to claim 1, wherein an included angle between each middle supporting section and each distal supporting section is in a range from 15 degrees to 90 degrees or 90 degrees to 165 degrees.

6. The left atrial appendage occluder according to claim 1, wherein the connection member is a flexible connection member or an elastic connection member.

7. The left atrial appendage occluder according to claim 6, wherein the connection member comprises a proximal connecting end, a distal connecting end, and a connecting rod connected between the proximal connecting end and the distal connecting end;

the proximal connecting end is connected with the sealing plate;

the distal connecting end is connected with the fixing frame;

the distal connecting end comprises a ball socket; and the distal end of the connecting rod comprises a ball head matched with the ball socket.

8. The left atrial appendage occluder according to claim 7, wherein the connecting rod is an elastic or flexible rod element, or is of a spring structure, or a woven structure.

9. The left atrial appendage occluder according to claim 7, wherein the connecting rod is a rod structure with a diameter of 0.1 mm to 5 mm.

10. The left atrial appendage occluder according to claim 7, wherein the ball head and the ball socket form a hinge mechanism.

11. The left atrial appendage occluder according to claim 10, wherein the ball head comprises a convex spherical surface facing to the ball socket, the ball socket comprises a concave spherical surface facing to the ball head; and the convex spherical surface is contained in the concave spherical surface to form a moveable connection.

12. The left atrial appendage occluder according to claim 10, wherein the ball head and the ball socket may rotate at any angle.

13. The left atrial appendage occluder according to claim 1, wherein the sealing plate is of a double filament woven structure.

14. The left atrial appendage occluder according to claim 1, wherein the number of the supporting rods is in a range from 3 to 6.

15. The left atrial appendage occluder according to claim 1, wherein the distal end of the second fixing connector of the fixing frame is a spherical structure.

16. The left atrial appendage occluder according to claim 1, wherein the film covers a whole outer surface of each of the middle supporting sections.

17. The left atrial appendage occluder according to claim 1, wherein the connection member and the fixing frame each comprises a proximal end and a distal end, and the distal end of the connection member is fixedly connected with the first fixing connector which is located at the proximal end of the fixing frame.

18. A left atrial appendage occluder, comprising:

a sealing plate, a fixing frame located on one side of the sealing plate, and a connection member for connecting the sealing plate with the fixing frame, wherein the fixing frame comprises a central longitudinal axis along which a first fixing connector and a second fixing connector are aligned and a plurality of supporting rods of not less than 3 arranged around the central longitudinal axis, the supporting rods having first ends and second ends;

the first ends of the supporting rods are gathered and fixed by the first fixing connector; the second ends of the supporting rods are gathered and fixed by the second fixing connector; and the connection member is connected with the first fixing connector;

wherein:

the sealing plate and the fixing frame each have a radial deformability and an axial deformability, and the radial deformability of the sealing plate is greater than that of the fixing frame such that under an action of a same radial force, a radial length variation of the sealing plate is greater than a radial length variation of the fixing frame or a radial length change rate of the sealing plate is greater than a radial length change rate of the fixing frame.

19. The left atrial appendage occluder according to claim 18, wherein the axial deformability of the sealing plate is greater than that of the fixing frame such that under an action of a same axial force, a displacement of the sealing plate along an axial force direction is greater than of the fixing frame along the axial force direction.

20. The left atrial appendage occluder according to claim 18, wherein each supporting rod comprises a proximal supporting section, a distal supporting section, and a middle supporting section connected between the proximal supporting section and the distal supporting section, and a film being positioned around the middle supporting sections along an outer diameter of the fixing frame and covering at least part of an outer surface of each middle supporting section.

\* \* \* \* \*